(12) United States Patent
Milin

(10) Patent No.: US 9,302,949 B2
(45) Date of Patent: Apr. 5, 2016

(54) SYSTEM FOR PROCESSING WASTE USING INSECT LARVAE

(76) Inventor: Ivan Milin, Toronto (CA)

( * ) Notice: Subject to any disclaimer, the term of this patent is extended or adjusted under 35 U.S.C. 154(b) by 1071 days.

(21) Appl. No.: 12/451,187

(22) PCT Filed: May 1, 2008

(86) PCT No.: PCT/CA2008/000825
§ 371 (c)(1),
(2), (4) Date: Oct. 29, 2009

(87) PCT Pub. No.: WO2008/134865
PCT Pub. Date: Nov. 13, 2008

(65) Prior Publication Data
US 2010/0129273 A1    May 27, 2010

(30) Foreign Application Priority Data

May 4, 2007   (CA) ...................................... 2587901

(51) Int. Cl.
*C05F 17/00* (2006.01)
*A01K 67/033* (2006.01)
*F26B 17/08* (2006.01)

(52) U.S. Cl.
CPC ........... *C05F 17/0009* (2013.01); *A01K 67/033* (2013.01); *F26B 17/08* (2013.01); *Y02P 20/145* (2015.11); *Y02W 30/43* (2015.05)

(58) Field of Classification Search
CPC .... C05F 17/0009; A01K 67/033; F26B 17/08
USPC ...................................................... 435/290.4
See application file for complete search history.

(56) References Cited

U.S. PATENT DOCUMENTS

| | | | | |
|---|---|---|---|---|
| 2,043,265 A | * | 6/1936 | Roeder | 210/609 |
| 3,961,603 A | * | 6/1976 | Gaddie, Sr. | 119/6.7 |
| 5,178,094 A | * | 1/1993 | Carr et al. | 119/6.5 |
| 5,725,083 A | * | 3/1998 | Archer | 198/499 |
| 5,759,224 A | * | 6/1998 | Olivier | 71/9 |
| 5,919,366 A | * | 7/1999 | Cameron | 210/602 |
| 6,780,637 B2 | * | 8/2004 | Olivier | 435/290.4 |

* cited by examiner

*Primary Examiner* — Jonathan Hurst
(74) *Attorney, Agent, or Firm* — Elias Borges

(57) ABSTRACT

The present invention is a system for processing organic waste using insect larvae, which has the advantage of being able to process large quantities of organic fecal waste material. The system includes a plurality of substantially flat reaction vessels stacked one on top of the other in parallel arrangement to form a processing blocks 11. Each of the reaction vessels in the processing block 11 are dimensioned and configured to contain a quantity of organic waste, each reaction vessel having front and back ends and side edges, the reaction vessels each being separated from the reaction vessel above by an air space 23, the processing block being contained in a plant enclosure having side walls. At least one of the side walls of the plant enclosure (plenum wall 38) is positioned adjacent the processing block such that the plenum wall is adjacent one of the side edges of the reaction vessels. The plenum wall has a plurality of openings which open to the air spaces and the openings positioned on the plenum walls such that openings are immediately adjacent air spaces. The system further includes an air circulation system for circulating purified and adjusted air through the air spaces by passing air through each of the openings in the plenum wall. The system also includes a feeder system for loading raw organic waste onto the reaction vessels and a discharge system for removing processed organic waste from the reaction vessels.

8 Claims, 7 Drawing Sheets

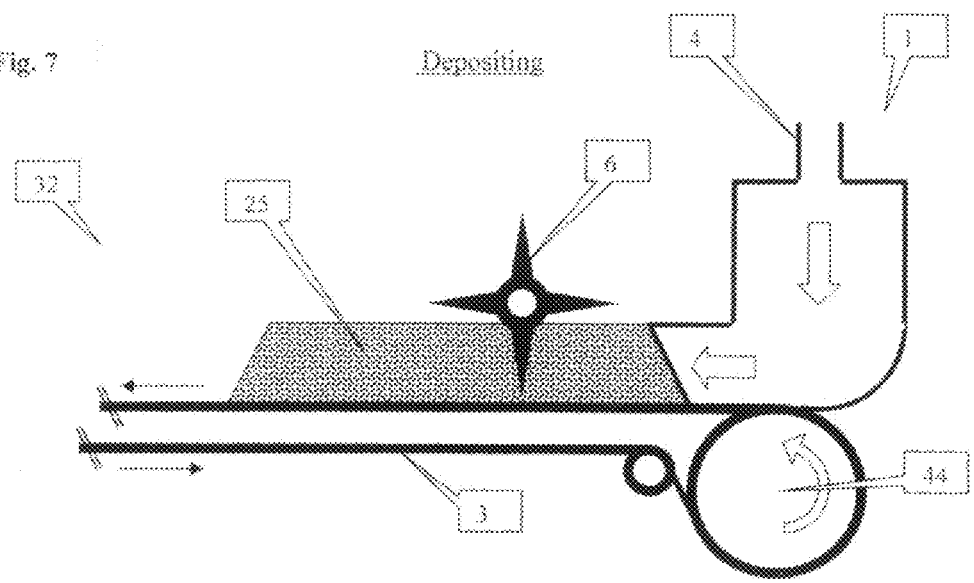
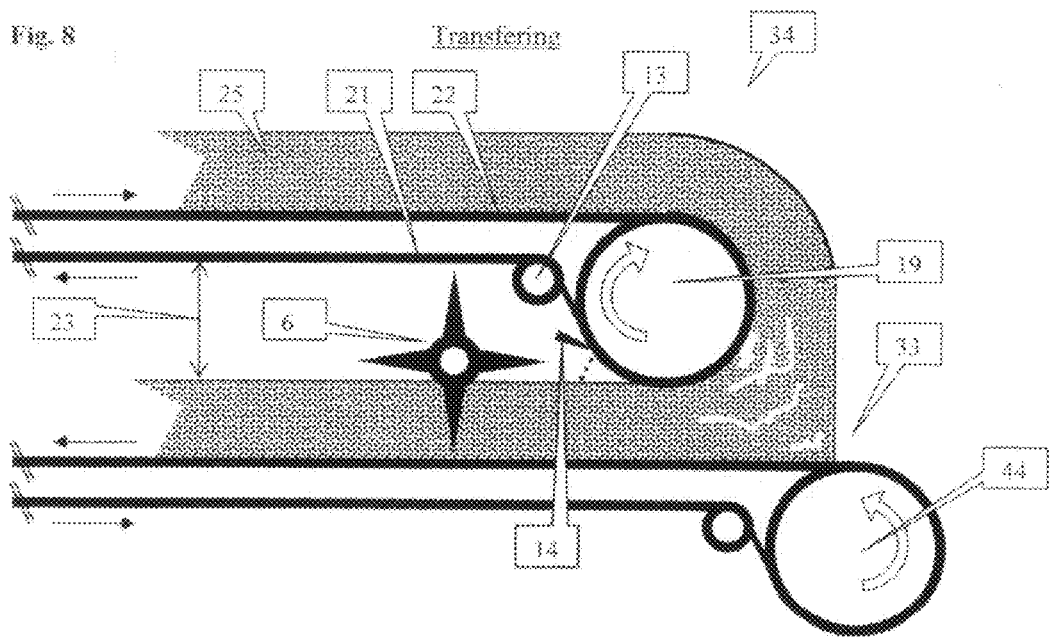

SYSTEM FOR PROCESSING WASTE USING INSECT LARVAE

FIELD OF THE INVENTION

The invention relates generally to processes for processing organic waste.

BACKGROUND OF THE INVENTION

As long as life existed, recycling was the way to balance the life cycle on this planet. We currently have the technology to recycle most of our waste, but most recycling technologies are not profitable and are therefore not likely to be implemented. In particular, the large scale processing and recycling of animal, bird and human feces, which is generated in enormous amounts on huge industrialized bird and animal farms, and in our own cities, is extremely problematic.

For hundreds of millions of years, flies have been depositing their larvae onto animal feces and in the process of feeding, the larvae where transforming the feces into the best natural, organic fertilizer known and larvae them self, become the protein-rich food for birds and animals.

Beside some laboratory and pilot-plant experiments, there are a few known attempts to design equipment and plant layout, which would use larvae of flies to process animal and bird feces. The attempts where somewhat successful in obtaining organic fertilizers and protein rich mass of larvae, but this technology was not used much because of sever technological problems encountered during production and due to a lack of profitability of the plants. A few different systems have been tested in this field. In one system, flies are simply allowed to deposit larvae on the pile of feces placed in a pit and mature larvae were collected as they try to migrate out of the pile, to start the process of pupating. Only a portion of feces close to the surface where transformed to the fertilizer and the rest of feces simply degraded anaerobic, releasing large amounts of ammonia, formaldehyde and other highly polluting green house gasses into the atmosphere. A huge infestation of flies tormented the neighborhoods and leakage from the pile polluted soil and water.

In an other system, feces ("substrate") is deposited directly onto a conveyer belt, seeded with larvae of flies and the conveyer itself is used as a reaction vessel. In another system, trays with substrate piled there on are seeded with fly larvae and are moved on conveyer belts through the process for several days, until the substrate was transformed into the organic fertilizer.

Attempts to use conveyer belts as a reaction vessel created many difficulties. One of the difficulties is that older larvae would migrate into the territory of younger larvae and compete with the younger larvae for the food, causing a food shortage for younger larvae, which would stay underdeveloped. On the other side, where older larvae migrated from, the substrate is left with not enough larvae to finish the process, so some substrate remained unprocessed. Also, a thick crust of dried out substrate, formed on the top of the processed material, could not be processed by larvae. The thick crust also prevents poisonous decomposition gasses from leaving the substrate. Removing the crust with scrapers is a very messy and costly procedure.

Also, conveyer belt systems, as used now, are very bulky, very messy, and require huge facilities but offers very low productivity (capacity per occupied area). The high cost of energy makes it very costly to maintain large facilities, especially in this industry, where the cost of heating and ventilation makes up a large portion of operating expenses.

Some improvements are made by placing 3 conveyer belts one on top other and using each level as a reaction vessel for one-day production. In such a system, two sets of 3 conveyers are used to finish the process of conversion. These triple conveyer systems solved the problem of older larvae migrating to the substrate of younger larvae, because in these triple conveyer systems all the larvae on one level are of the same age.

Using triple conveyer systems created new problems. Within the triple conveyer system, as they are now, heating and ventilation problems where solved by placing the conveyers within the long tunnels and blowing warm air along the tunnels. If the air flow along the tunnel is slow, the end of the tunnel never gets sufficient ventilation but if the air speed along the tunnel is too fast, the substrate at the beginning of the tunnel gets very dry and larvae could not process it. To decrease the speed of air and get sufficient air flow at the same time, the size of the tunnel had to be enlarged to the height of 60 cm to 70 cm, making it very messy and difficult to contain and control the substrate when dropping from that height and at the same time making the whole system very bulky and inefficient. The length of the tunnel should normally increase the capacity and efficiency of the system, but the longer the tunnel gets, the higher it has to be to obtain the proper ventilation, which unfortunately increases bulkiness and decreases efficiency. Ventilation along the tunnel was definitely problematic.

The moving tray system is similar to the conveyer belt system but instead of loading the substrate directly onto a conveyer belt, the substrate is loaded into a plurality of trays and the trays are placed onto the conveyer belt creating similar ventilation problems. In a tray based system, older larvae could not migrate to the trays with younger larvae but they also could not get out of the substrate after the process is finished. Also, this design does not lend itself to a multi-layer or stacked design, so the process is much bulkier and less productive.

Static trays have also been suggested for use with this technology. Unfortunately, filling, emptying, cleaning and handling large amounts of trays is very difficult and costly, for any system using trays. Furthermore, the ventilation and formation of dry crust where not solved in any of the tray systems as well. As a result of everything, tray systems, as they are now, are very costly, and problematic, acceptable only for small laboratory operations.

None of the above processes utilizes an efficient and economical solution for heating and ventilation of processing facilities, which represent a good portion of operating expenses.

Preheating of substrate was also not solved efficiently in any of the prior existing processes, resulting in more degradation and more decomposition products, requiring additional ventilation during the processing. The prior art calls for preheating of the substrate within the receiving tank, which is acceptable for the smaller quantities, but not so practical in case of larger tanks and larger quantities of substrate. Small quantity of substrate could be preheated in a few hours with the use of heaters placed on the outside surfaces of a smaller substrate receiving tank, but for a larger amount of substrate in colder climates, heating within the receiving tank, from the outside of the tank, could take days to reach the suitable working temperature. High temperatures could not be used to speed up the heating within the large tanks, because mixing in large tanks could never be good enough to prevent drying or burning of substrate on the heated surfaces. The gasses from burned substrate would require even more ventilation.

Preheating the entire substrate within the larger tanks also increases the speed of decomposition of the entire mass of substrate producing much more decomposition gasses what would again require more vigorous ventilation during the processing. Also, mixing the old substrate with the fresh one would increase the decomposition of the fresh substrate by introducing a decay causing bacteria from the old substrate. Preheated and seeded with decay-causing bacteria, the entire mass of substrate would decay rapidly releasing ammonia, formaldehyde and other poisonous gasses, again requiring additional and more vigorous ventilation during the processing.

Given the numerous drawbacks of the prior art systems of substrate processing, improved systems are desirable. The improved system would overcome the problems of low productivity, poor and expensive heating & ventilation, mixing and preheating of entire substrate within the tank and others. All of the improvements would lead to sufficient profitability and thus, acceptance of this technology by the industry.

SUMMARY OF THE INVENTION

The present invention is a system for processing organic waste using insect larvae which overcomes the disadvantages of the prior art. The system includes a plurality of substantially flat reaction vessels stacked one on top of the other, to form a processing block 11. Each of the reaction vessels in the processing block is dimensioned and configured to contain a quantity of organic waste and each reaction vessel has front and back ends and side edges. Each of the reaction vessels is separated from the reaction vessel above by an air space and the processing block is contained in a plant enclosure having side walls. At least one of the side walls of the plant enclosure (plenum wall 38) is positioned adjacent the processing block such that the plenum wall is adjacent one of the side edges of the reaction vessels. The plenum wall has a plurality of openings which communicate with the air spaces. The openings are positioned on the plenum wall such that the openings are immediately adjacent the air spaces. The system further includes an air circulation system for circulating air through the air spaces by passing air through the openings in the plenum wall and a feeder system for loading raw organic waste onto the reaction vessels. The reaction vessels preferably being an elongated belt, which consists of an elongated flexible web 3 suspended between a pair of rollers.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention.

DESCRIPTION OF THE DRAWINGS

FIG. 7 is a cross-sectional view of the loading end portion of the topmost conveyor belt of the present invention during the operation of depositing substrate, and showing a side view of the perforator portion of the invention.

FIG. 8 is a cross-sectional view of a loading end of a conveyor belt during the operation of transferring substrate, and showing a side view of the perforator portion of the invention.

In the drawings like characters of reference indicate corresponding parts in the different figures.

DETAILED DESCRIPTION OF THE INVENTION

Figure 1:
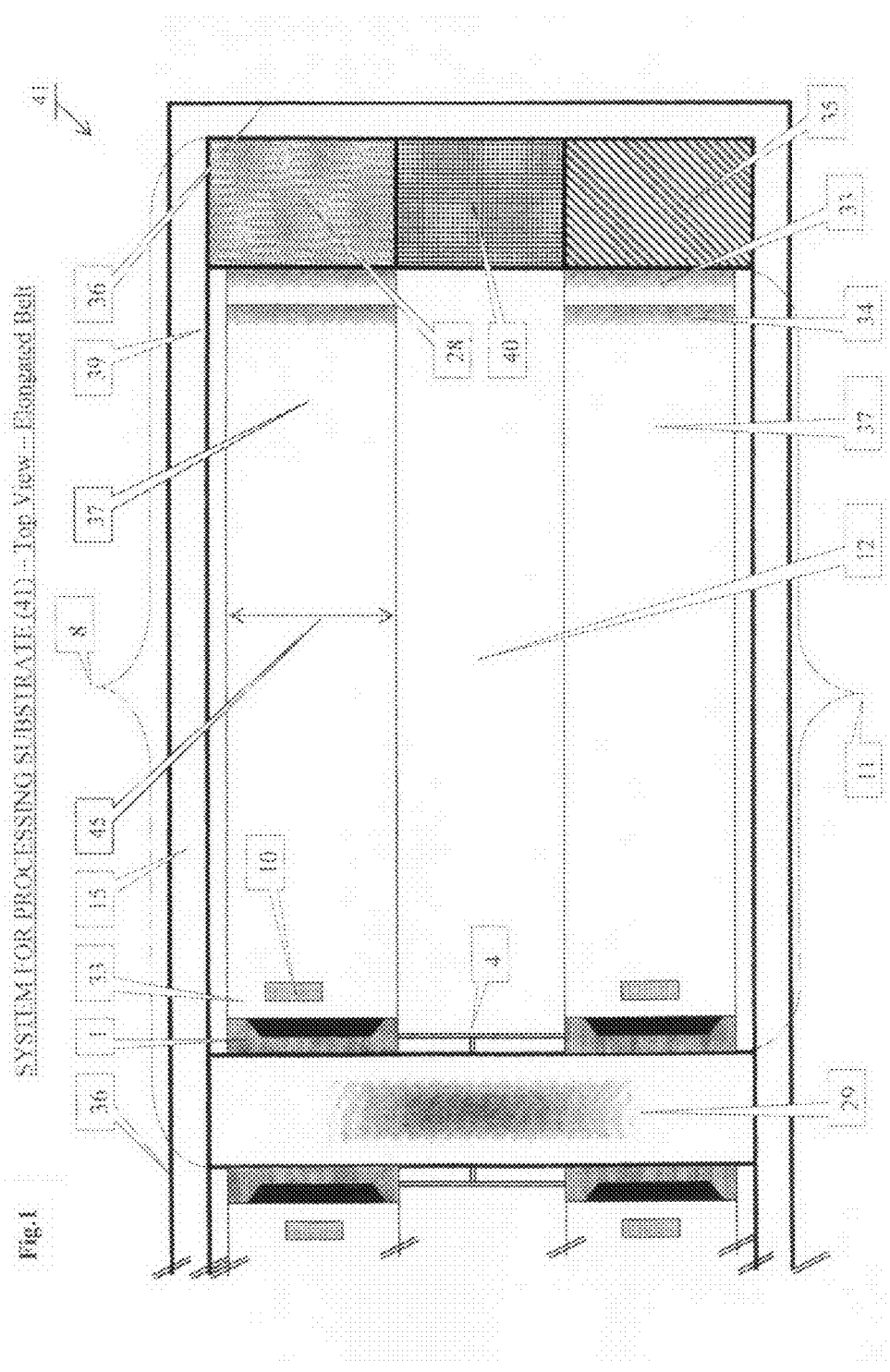
FIG. 1 is a schematic top view of a system for processing substrate according to the present invention showing the various components of the system arranged in a rectangular arrangement.
Figure 2:
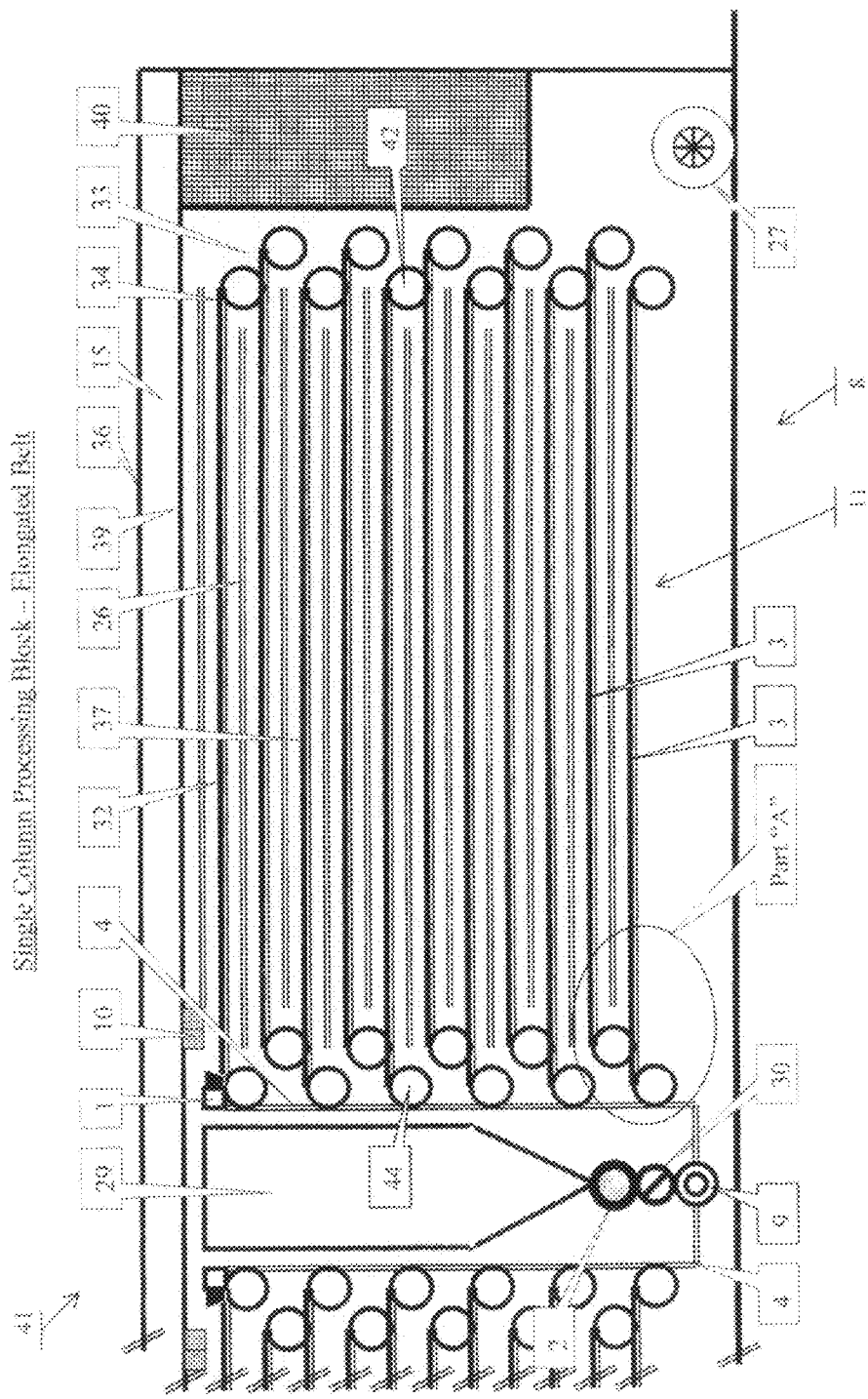
FIG. 2 is side view from the center of the system shown in FIG. 1, showing the stacked arrangement of reaction vessels (elongated belts 37), in a single column processing block.
Figure 3:
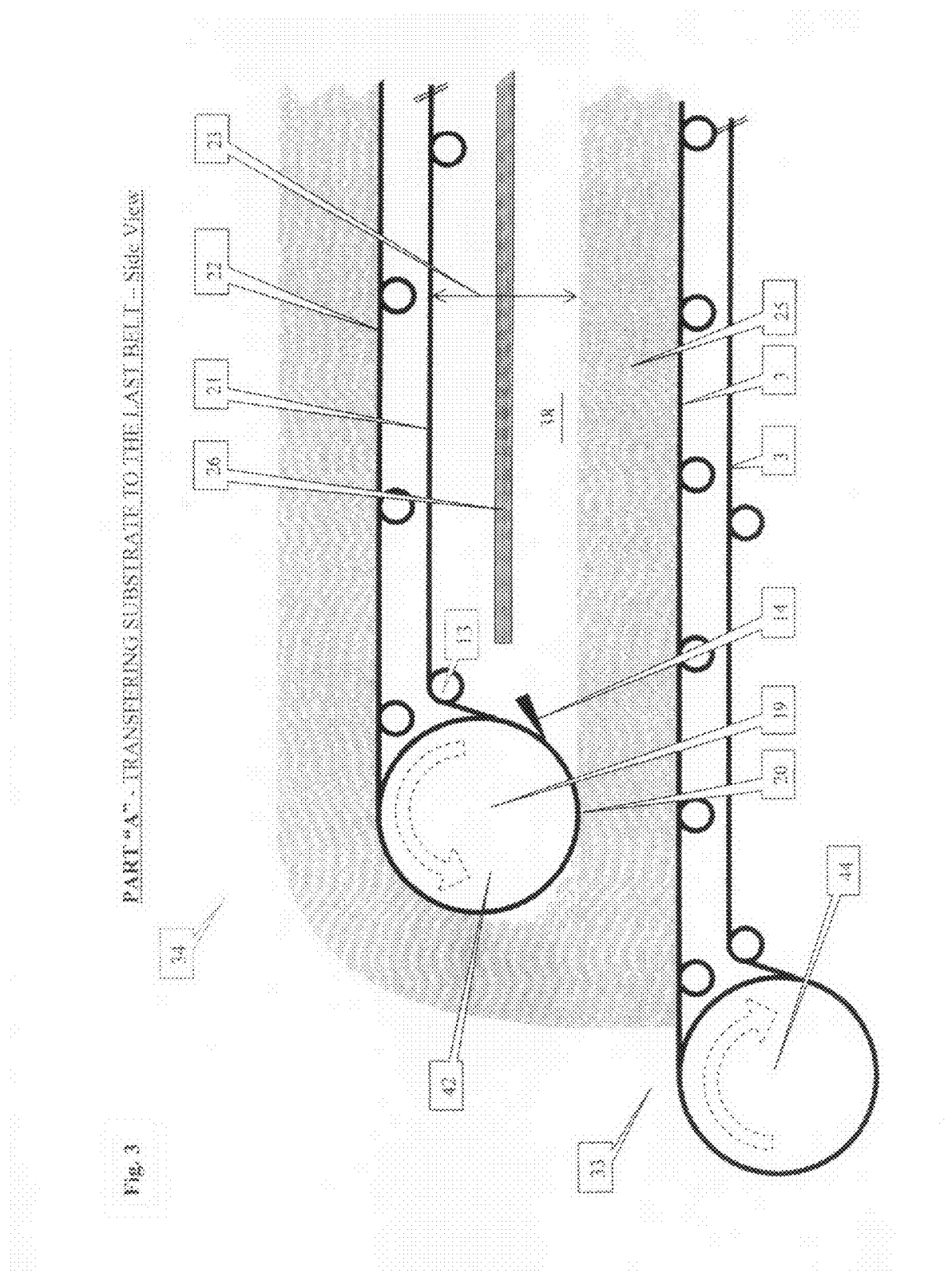
FIG. 3 is an expanded view of part A of FIG. 2, showing the end portions of a pair of elongated belts during the substrate transfer, with a web scraper 14.

Referring firstly to FIGS. 1 and 2, a system (or plant) for processing organic waste by insect larvae made in accordance with the present invention, is shown generally as item 41, and consists of one or more independent production sections 8 coupled to mutual substrate receiving tank 29 in the middle. The production sections 8 are each placed on one side of the mutual substrate receiving tank 29 and consists of one or more processing blocks 11, plus finishing and air treating equipment placed on the periphery of the plant, opposite of receiving tank 29. Referring to FIG. 2, processing blocks 11 each consist of a plurality of substantially flat reaction vessels arranged in parallel stacks one above the other, in a row containing one or more stacks adjacent to each other. Preferably, the reaction vessels each consists of a elongated belt 37, which are stacked as a single column, in a staggered arrangement on the top of each other such that the unloading end 34 of one elongated belt would be immediately above the loading end 33 of the elongated belt placed below it. Each belt 37 is made of an elongated flexible web 3 which is suspended (looped) onto a pair of rollers 42 and 44, with roller 42 being an "unloading" roller located at the unloading end 34 and roller 44 being a "loading" roller which is located at the loading end 33. As best seen in FIG. 3, the looped web 3 has upper portion 22 that holds the substrate and lower portion 21. Each belt 37 is elongated and has a width (see item 45 in FIG. 1) which will preferably be between 2 to 4 feet, or there about. Each belt will have a length as defined by rollers 42 and 44 which will be far greater than its width, generally in the range of about 50 feet to about 500 feet.

Referring back to FIG. 2, each processing block includes a substrate depositor 1 and seeder 10, which are positioned above the loading end 33 of the topmost elongated belt 32. Seeder 10 is a device configured to deposit a predetermined amount of fly eggs on the organic substrate as the topmost elongated belt 32 passes underneath it.

From the receiving tank 29, the substrate is moved by the moving device 30, through the substrate mixer-homogenizer 2, and a substrate heater 9, all located outside of the receiving tank 29, to the depositor 1. Distributing pipes 4 deliver the homogenized and preheated substrate to depositors.

Figure 5:
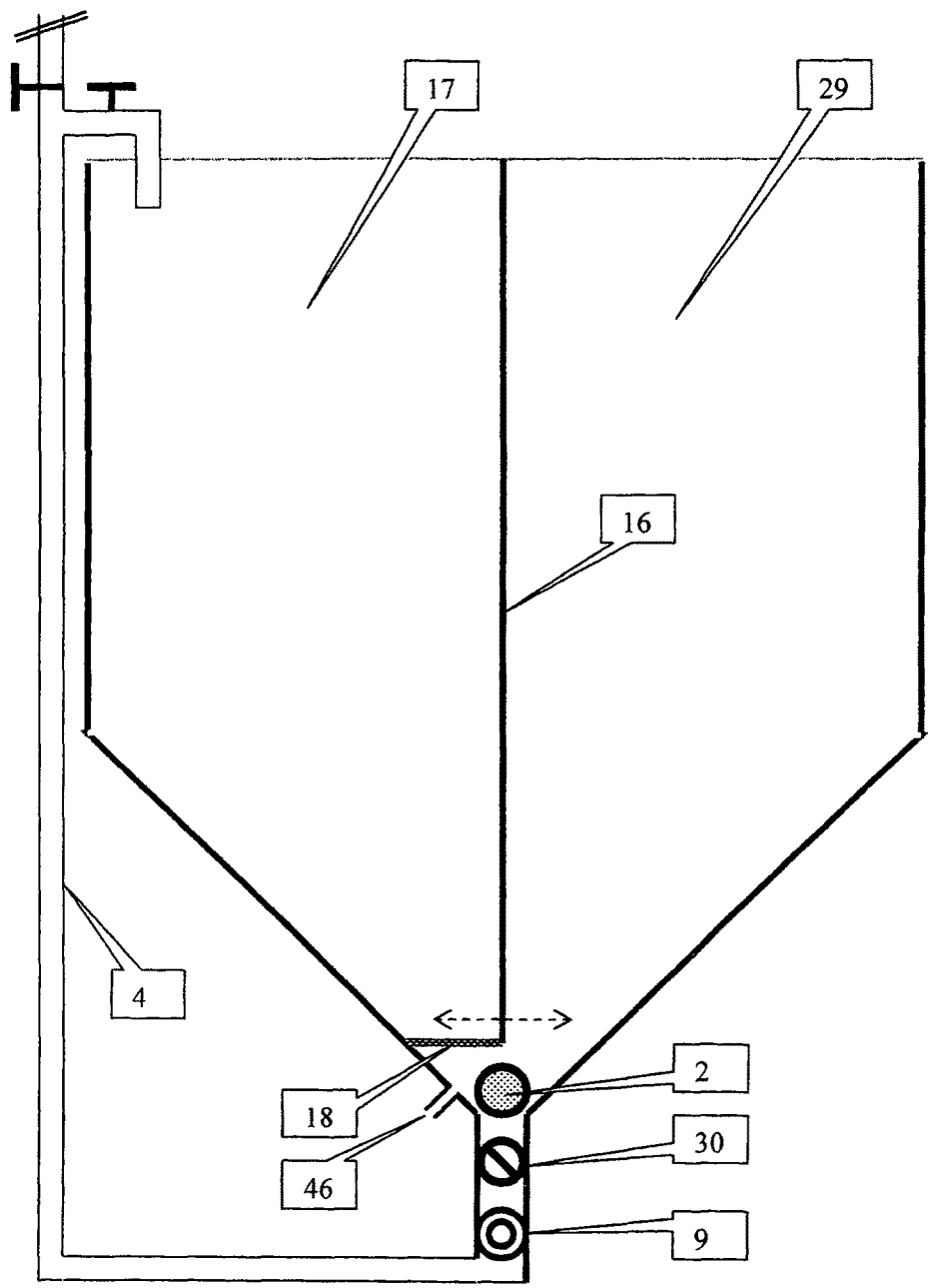
FIG. 5 is a schematic side view of the feeder system including a receiving tank 29 and precondition tank 17, of the present invention.
Figure 6:
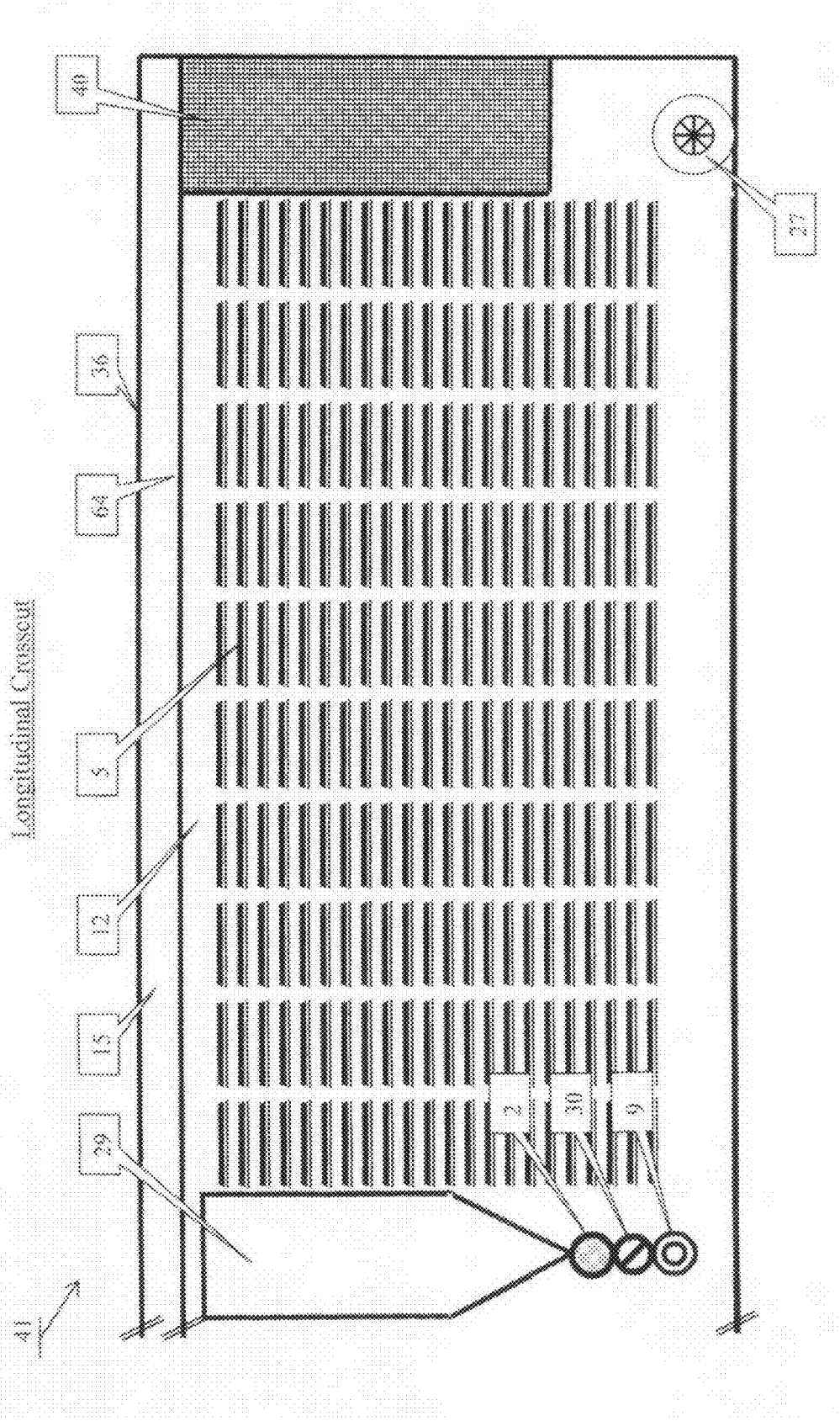
FIG. 6 is side view of an alternate embodiment of the present invention wherein the rows of flat reaction vessels 5 form a processing block.

Referring now to FIG. 5, when the substrate is not needed to the depositor, some preconditioned substrate is delivered to the preconditioned tank 17. Having some preconditioned substrate ready for use eliminates the need for heating and mixing the entire substrate of the receiving tank. The heating and mixing of substrate within the receiving tank is not desirable because of technical difficulties and much faster degradation of warm substrate, requiring more vigorous ventilation during processing. The one way to make a precondition tank is to divide a larger tank in two compartments with divider 16 and provide the directional valve 18.

Referring back to FIG. 2, one or more times a day, substrate with larvae is transferred from upper elongated belt to the one below and left there for the larvae to process it. The number of elongated belts is adjusted so when the substrate reaches the last elongated belt, the larvae have finished processing the substrate into organic fertilizer, which is then transported to the sieving station and further for drying palletizing and packaging.

The bottom portion of the sieving station 40 contains a ventilation fan 27. As seen in FIG. 1, air treating system 28 is placed beside the sieving station and is connected to the ventilation fan 27. The air treating system is designed to purify the air and adjust the relative humidity and temperature of the air for optimal larvae growth. Suitable air purifiers, heaters and humidifiers are readily available in the marketplace which can be used to form the air treating system. Drying station 35 is placed on the other side of sieving station 40, on the end of processing block 11.

Figure 4:
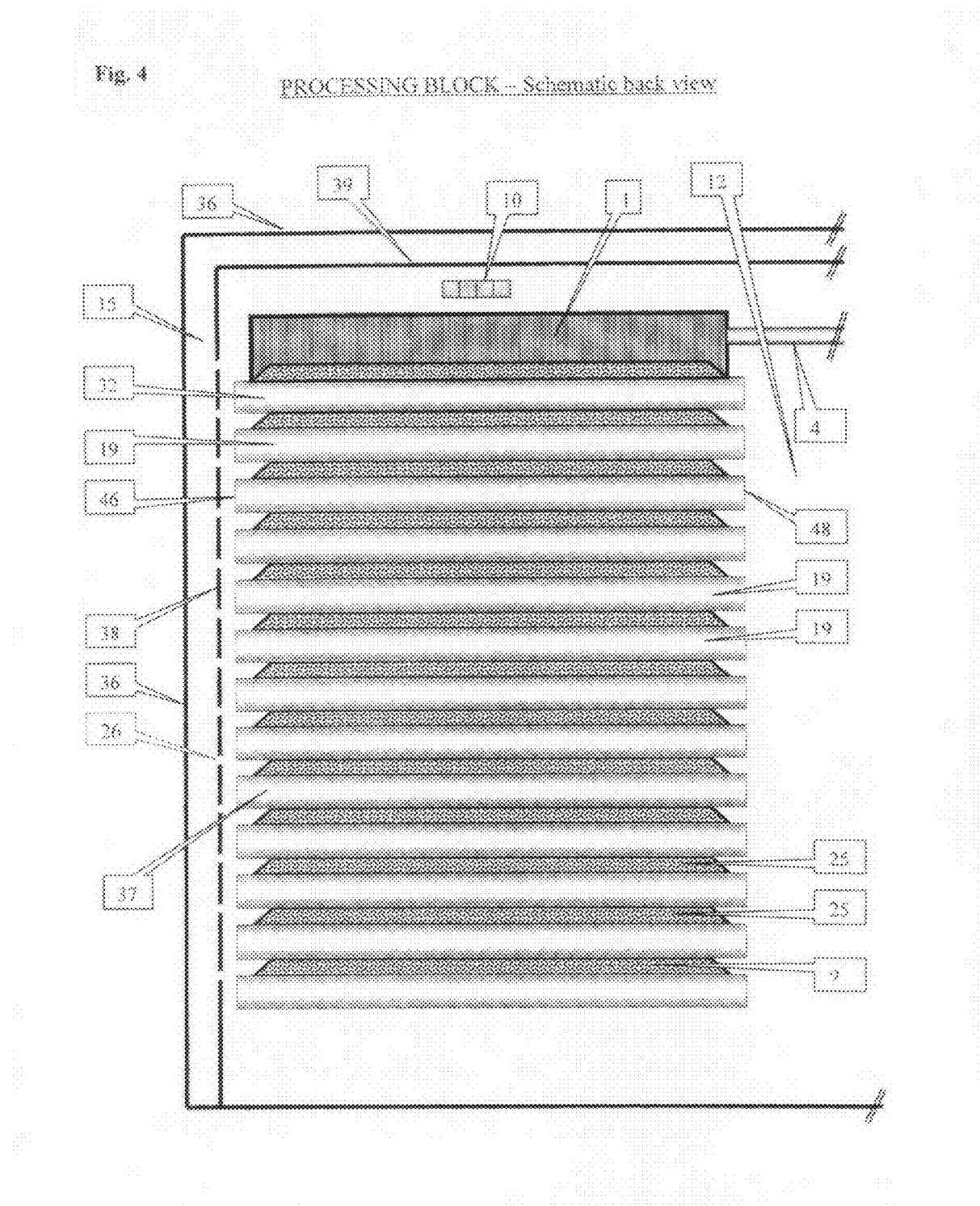
FIG. 4 is a schematic back view of a processing block made in accordance with the present invention and showing the relationship of the stacked elongated belts 37 to the enclosures and openings 26.

Referring now to FIG. 4, the entire plant is completely enclosed within a plant enclosure 39, creating interior space 12, which is in turn further enclosed within the exterior enclosure 36, thereby creating exterior space 15. Ventilation fan 27 (see FIG. 2) is configured to draw air from inside of the plant enclosure 39 and push the air through the air treating system 28 (FIG. 1) into the exterior space 15, thereby creating negative pressure within interior space 12 and positive pressure within the exterior space 15. Plant enclosure 39 forms a plenum wall 38 adjacent elongated belts 37 and having a plurality of horizontal openings 26, which are strategically located on the plenum wall 38 immediately adjacent the air space 23 between adjacent reaction vessels (elongated belts 37), just where the deposited substrate 25 is. As the air pressure within the plant enclosure 39 is lowered, purified and conditioned air is sucked from the outside of plant enclosure 39, through openings 26 and into air spaces 23 where the substrate and larvae are located. Hence, the air flows across the width of reaction vessels 37 as opposed to along the length of it.

Referring now to FIG. 3, to create some room for ventilation, the lower portion 21 of the web 3 is lifted as much as possible by the small web supports 13, creating relatively thin space 23 above the substrate 25. For the ventilation to be efficient in a narrow space like that, a uniform airflow, across the substrate has to be achieved for the entire length of the deposited substrate. Openings 26 are provided along the plenum wall 38 adjacent air spaces 23.

Referring back to FIG. 2, to create a sufficient, uniform and precise air flow through the openings 26 in the plenum wall, a ventilation fan 27 is placed within the plant enclosure 39, and is configured to suck air from the plant enclosure and pass it through an air treating system 28 (see FIG. 1). The ventilation fan creates a partial vacuum within the plant enclosure, which sucks the air from surroundings of the plant, trough the openings 26 and create the needed uniform airflow over the substrate. This very simple solution has many advantages over traditional ventilation systems. An important economic advantage is that expensive installation of ventilation ducts are not needed at all.

Beside economic advantages, there are other advantages worth mentioning. Helped by perforations within the deposited substrate, the partial vacuum, created within the plant interior, would suck toxic decomposition gasses (ammonia, formaldehyde, and others) out of the substrate, creating better environment for larvae growth. Lowered amounts of toxic decomposition gasses within the substrate would allow larvae to feed deeper within the substrate, which means the thickness of substrate could be increased, increasing the productivity of the plant and making it more profitable.

Referring now to FIG. 5, when the organic waste to be processed is deposited into the receiving tank 29, it becomes a "substrate". To avoid mixing and heating of the substrate within the large receiving tanks, a small but efficient mixer-homogenizer and substrate heater are connected to the distributing pipes 4, between the receiving tank and depositor. Heating and mixing only the portion of the substrate which is being moved from the receiving tank and leaving the rest of the substrate cold and undisturbed, greatly reduces the degradation of substrate, lowering the amount of odor and toxic gasses within the substrate. Placing the substrate heater 9 and mixer-homogenizer 2 outside of the tank, within the distributing pipes 4, dramatically reduces the need for vigorous ventilation around the reaction vessels.

An inlet 46 is preferably placed before the mixer-homogenizer and configured to permit adding of ingredients into the substrate. If the required ventilation levels would dry the substrate beyond the moisture level needed for proper growth of larvae, water must be added to the substrate via inlet 46, before the introduction of larvae.

Referring now to FIG. 7, after the substrate 25 is heated to the needed temperature, the distributing pipes 4 will deliver the substrate to the substrate depositor 1. Depositor 1 is positioned above loading end of the topmost elongated belt 32. The belt moves along as substrate is deposited onto the belt. After the substrate has been deposited along the whole length of the elongated belt, the elongated belt would stop moving and the depositor would stop depositing. To improve ventilation in the substrate 25, circular perforator 6 is strategically placed near the loading end to create holes and channels within the deposited substrate. Preferably, perforator 6 is placed just after depositor 1 and also adjacent roller 44 to permit the formation of ventilation channels right after depositing or transferring of substrate.

Referring back to FIG. 3, prior art methods suggests separate "spreading rollers" to spread and distribute fallen substrate evenly after it falls from an upper elongated belt to a lower one. With the present invention, a special roller is not needed because the upper roller 19 is placed so close to the elongated belt below, that it could act as spreading roller as well. By placing the elongated belts so close to each other, the height of the fall of substrate is reduced substantially and it is much easier to control the falling substrate and keep the area clean. Since the elongated belts in this invention are modified to allow for across ventilation, the vertical distance between two elongated belts could be minimized to the thickness of the substrate itself.

In order to create some air space for ventilation, web support 13 is positioned below the lower portion 21 as close as possible to the upper portion 22, lifting the lower portion 21 immediately adjacent roller 19 (also shown as item 42), creating the necessary air space for ventilation. By forcing the lower portion of the web upwards, the place for positioning a web scraper 14 is also created. Web scraper is positioned such that it bears against web 3 on the lower portion 21, adjacent or just after the bottom point 20 of the unloading roller 19 and adjacent the point where the belt comes off roller 19, so that the web will be cleaned after the roller distributes and spreads the fallen substrate.

Referring now to the FIG. 1, to make the air flow more efficient and to prevent a warm and conditioned air to simply be vented to the atmosphere, a secondary exterior enclosure 36 was provided around the plant enclosure 39. The ventilation fan 27 (see FIG. 2) can now push the air through the air treating system 28 to the exterior enclosure 36 and create the positive air pressure in the space between two enclosures (exterior space 15). With positive pressure on the outside of the plant and the negative pressure inside the plant, the sufficient airflow through the openings 26 could be achieved with much less power.

The present invention has many advantages over the prior art. Since the heating and ventilation of large and bulky facilities is very costly and represents a large portion of expenditure in this technology, the biggest challenge of this innovation was to compress the processing space as much as possible and yet have sufficient and uniform flow of properly conditioned and purified air across the reaction vessels, for optimal development and living conditions of fly larvae.

In the previous art, heating and ventilation was achieved by blowing heated air along relatively long tunnels in which the conveyer belt was placed. As a result, the beginning of the tunnel was vented vigorously with the substrate drying up more then needed, making it impossible for larvae to process it, while the opposite end of the tunnel was poorly ventilated with air already saturated with decomposition gasses and moisture from the rest of the tunnel. To achieve the proper ventilation on the opposite end of the tunnel, unreasonably large amounts of warm air had to be blown along the tunnel. According to the prior art, to reduce the drying of the substrate in the beginning of the tunnel, the speed of the air within the tunnel has to be reduced and to maintain enough fresh air for the end of the tunnel, the amount of passed air has to be increased. To satisfy both requirements over the 50 ft. tunnel, it was necessary to maintain a distance of 60 cm to 70 cm between the substrate and the ceiling of a tunnel, which made the whole system very bulky, low in productivity and expensive to run. A large amount of energy was used that way and most of it was vented out.

The large space needed for proper ventilation in prior art systems created other problems as well. During the transfer of substrate to the lower conveyer belt, substrate would have to fall from the height of the tunnel plus the conveyer system (at least 85 cm), which made the operation very messy and difficult to control. Indeed, everything in the previous art suggests a huge expenditure of energy, large processing facilities and great difficulty in controlling falling substrate and larvae from one level to other.

For the reasons stated above, in the present invention, instead of blowing the air along the long tunnel, the air was passed sideways, across the width of the elongated belt or across the row of reaction vessels, which is a much shorter distance (2-4 ft.). There is no need for a large volume of air or high speed of air because there is no significant difference between air quality on two sides across the width of the elongated belt or row of reaction vessels. Cross ventilation solves all of the problems mentioned above and dramatically reduces the space and energy requirements.

A specific embodiment of the present invention has been disclosed; however, several variations of the disclosed embodiment could be envisioned as within the scope of this invention. It is to be understood that the present invention is not limited to the embodiments described above, but encompasses any and all embodiments within the scope of the following claims.

Therefore, what is claimed is:

1. A system for processing organic waste using insect larvae comprising:
    a. a plurality of substantially flat conveyor belts stacked one on top of the other in a substantially parallel arrangement to form a first processing block, each of the conveyor belts in the first processing block being dimensioned and configured to contain a quantity of organic waste, each conveyor belt having front and back ends, opposite first and second side edges, a top surface, a bottom surface, a length and a width;
    b. the conveyor belts each being separated from the conveyor belts above by an unobstructed air space extending continuously between the top surface of the conveyor belts below and the bottom surface of the conveyor belts above along the length of each conveyor belt, each conveyor belt together with its air space and any organic waste therein forming a processing layer, each air space extending upwards between the opposite side edges of the conveyor belt below;
    c. the first processing block being contained in a plant enclosure having a plenum wall; the plenum wall positioned adjacent the first processing block such that the plenum wall is immediately adjacent the first side edges of the conveyor belts;
    d. the plenum wall having a plurality of openings which open to the air spaces, the openings positioned on the plenum walls such that the openings are immediately adjacent the air spaces, each opening being dimensioned and configured to allow passage of a need amount of air flow to the corresponding processing layer of the first processing block, each opening extending along the length of the conveyor belts;
    e. an air circulation system for circulating air between the opposite side edges of the conveyor belts by passing the air through the openings in the plenum wall, then through the air spaces and across the width of each conveyor belt;
    f. a feeder system for loading raw organic waste onto the conveyor belts, and
    g. a discharge system for removing the organic waste from the conveyor belts.

2. The system for processing organic waste using insect larvae defined in claim 1 wherein a second processing block is positioned beside the first processing block in a substantially parallel arrangement, the second processing block being contained within the plant enclosure and configured to be a substantially mirror image of the first processing block, the first and second processing blocks being separated by a central air passage; a second plenum wall formed within the plant enclosure, the second plenum wall positioned adjacent the second processing block such that the second plenum wall is adjacent the first side edges of the conveyor belts forming the second processing block, the second plenum wall having a plurality of openings which open to the air spaces in the second processing block, the openings positioned on the second plenum wall such that the openings are immediately the air spaces of the second processing block; each opening in the second plenum wall positioned such that the opening is continuous with the air space in the second processing block, the openings in the second plenum wall extending along the length of the conveyor belts in the second processing block between their front and back ends; each opening in the plenum wall and second plenum wall being dimensioned and configured to allow passage of a needed amount of air flow directly into the corresponding processing layer; the air circulation system being further configured to circulate air between the opposite side edges of the conveyor belts by passing the air through the openings in the plenum wall and the second plenum wall, and then through the air spaces and across the width of each conveyor belt in the first and second processing block.

3. The system for processing organic waste using insect larvae defined in claim 2 wherein the conveyor belts comprise rows of flat reaction vessels.

4. A system for processing organic waste using insect larvae comprising:
   a. a plurality of substantially flat conveyor belts stacked one on top of the other in a substantially parallel arrangement to form a first processing block, each of the conveyor belts in the first processing block being dimensioned and configured to contain a quantity of organic waste, each conveyor belts having front and back ends, side edges, a top surface, a bottom surface, a length and a width;
   b. the conveyor belts each being separated from the conveyor belt above by an air space extending continuously between the top surface of the conveyor belt below and the bottom surface of the conveyor belt above, and above the top surface of the conveyor belt topmost in the first processing block, the air space extending between the opposite side edges of the conveyor belts below and along the length of each conveyor belt, each conveyor belt together with its air space and any organic waste therein forming a processing layer;
   c. the first processing block being contained in a plant enclosure having a plenum wall; the plenum wall positioned adjacent the first processing block such that the plenum wall is adjacent the first processing block;
   d. the plenum wall having a plurality of openings which open to the air spaces, the openings positioned on the plenum walls such that openings are immediately adjacent the air spaces; each opening positioned between two adjacent conveyor belts and above the top surface of the conveyor belt topmost in the first processing block such that the opening is continuous with the air space, the openings extending along the length of the conveyor belts between the front and back ends, each opening being dimensioned and configured to allow passage of a needed amount of air flow directly into its corresponding processing layer of the first processing block;
   e. an air circulation system for circulating air between the opposite side edges of the conveyor belts by passing the air through the openings in the plenum wall, then through the air spaces and across the width of each conveyor belt;
   f. a feeder system for loading raw organic waste onto the conveyor belts, and;
   g. a discharge system for removing the organic waste from the conveyor belts.

5. The system for processing organic waste using insect larvae defined in claim 4 wherein a second processing block is positioned in a substantially parallel arrangement beside the first processing block, the second processing block being configured to be substantially a mirror image of the first processing block, the first and second processing blocks being separated by a central air passage; a second plenum wall formed within the plant enclosure, the second plenum wall positioned adjacent the second processing block such that the second plenum wall is adjacent the first side edges of the conveyor belts forming the second processing block, the second plenum wall having a plurality of openings which open to the air spaces in the second processing block, the opening positioned on the second plenum wall such that the openings are immediately adjacent the air spaces of the second processing block; each opening in the second plenum wall positioned such that the opening is continuous with the air space separating adjacent conveyor belts in the second processing block and above the conveyor belt topmost in the processing block, the openings in the second plenum wall extending along the length of the conveyor belts in the second processing block between their front and back ends; each opening in the plenum wall and second plenum wall being dimensioned and configured to allow passage of a needed amount of air directly into the corresponding processing layer; the air circulation system being further configured to circulate air between the opposite side edges of the conveyor belts by passing the air through the openings in the plenum wall and the second plenum wall, then through the air spaces and across the width of each conveyor belt in the first and second processing block.

6. The system for processing organic waste using insect larvae defined in claim 4 wherein the conveyor belts comprise rows of flat reaction vessels.

7. A system for processing organic waste using insect larvae comprising:
   a) a plurality of substantially flat conveyor belts stacked one on top of the other in a substantially parallel arrangement, each conveyor belt having opposite first and second side-edges and a substantially solid bottom for holding organic waste, the conveyor belts each being separated from the conveyor belts immediately above by an air space, the air space being immediately above the organic waste, the air space having a first side-surface and an opposite second side-surface and a thickness, the first side-surface extending upwards from the first side-edge and second side-surface extending upwards from the second side-edge, the conveyor belt together with its air space and organic waste form a processing layer, the processing layers stacked one on top of the other to form a processing block;
   b) each of the conveyor belts in the processing block being dimensioned and configured to contain a quantity of organic waste; the processing block being contained in a plant enclosure having a plenum wall, the plenum wall positioned adjacent the processing block such that the plenum wall is adjacent one of the side-edges of the reaction vessels;
   c) the plenum wall having a plurality of openings which open to the air spaces; the openings positioned on the plenum walls such that the openings are immediately adjacent the air spaces; each opening being positioned above the solid bottom of the conveyor belts to allow the passage of air from the one side of the plenum wall into the corresponding air space, each opening positioned such that the opening is continuous with the air spaces, each opening being dimensioned and configured to allow passage of a needed amount of air flow directly into the corresponding processing layer of the processing block.

8. The system for processing organic waste using insect larvae defined in claim 7 wherein the conveyor belts comprise rows of flat reaction vessels.

* * * * *